(12) United States Patent
Sokol et al.

(10) Patent No.: US 7,735,377 B1
(45) Date of Patent: Jun. 15, 2010

(54) LASER BOND INSPECTION USING ANNULAR LASER BEAM

(75) Inventors: David W. Sokol, Dublin, OH (US);
Craig T. Walters, Powell, OH (US);
Steven M. Toller, Dublin, OH (US);
Richard H. Bossi, Renton, WA (US);
Kevin R. Housen, Tacoma, WA (US)

(73) Assignees: LSP Technologies, Inc., Dublin, OH (US); The Boeing Company, Chicago, IL (US)

( * ) Notice: Subject to any disclaimer, the term of this patent is extended or adjusted under 35 U.S.C. 154(b) by 0 days.

(21) Appl. No.: 12/396,081

(22) Filed: Mar. 2, 2009

Related U.S. Application Data (63) Continuation of application No. 11/873,677, filed on Oct. 17, 2007, now Pat. No. 7,509,876.

(51) Int. Cl.
*G01N 3/08* (2006.01)
(52) U.S. Cl. ..................................... 73/827
(58) Field of Classification Search ............... 73/150 A, 73/588, 827
See application file for complete search history.

(56) References Cited

U.S. PATENT DOCUMENTS

| | | | |
|---|---|---|---|
| 4,004,456 A | 1/1977 | Vahaviolos |
| 4,207,771 A | 6/1980 | Carlos et al. |
| 4,401,477 A | 8/1983 | Clauer et al. |
| 4,545,018 A | 10/1985 | Clements et al. |
| 4,824,250 A | 4/1989 | Newman |
| 4,838,085 A | 6/1989 | Pellerin et al. |
| 4,901,357 A | 2/1990 | Albright |
| 5,127,019 A | 6/1992 | Epstein et al. |
| 5,269,778 A | 12/1993 | Rink et al. |
| 5,473,315 A | 12/1995 | Holroyd |
| 5,572,016 A | 11/1996 | Wood et al. |
| 5,729,012 A | 3/1998 | Wood et al. |
| 5,803,965 A | 9/1998 | Yoon |
| 5,965,877 A | 10/1999 | Wood et al. |
| 6,008,887 A | 12/1999 | Klein et al. |
| 6,238,187 B1 | 5/2001 | Dulaney et al. |
| 6,282,964 B1 | 9/2001 | Hancock et al. |
| 6,288,358 B1 | 9/2001 | Dulaney et al. |
| 6,373,876 B1 | 4/2002 | Dulaney et al. |
| 6,479,790 B1 | 11/2002 | Graham et al. |
| 6,512,584 B1 | 1/2003 | O'Loughlin et al. |
| 6,554,921 B2 | 4/2003 | Sokol et al. |
| 6,657,160 B2 | 12/2003 | Hackel et al. |

(Continued)

FOREIGN PATENT DOCUMENTS

GB 2225427 A 5/1990

OTHER PUBLICATIONS

Applicant notes the existence of associated, co-pending application, Sokol, et al., U.S. Appl. No. 10/950,865, filed Sep. 27, 2004.

(Continued)

*Primary Examiner*—Lisa M Caputo
*Assistant Examiner*—Freddie Kirkland, III
(74) *Attorney, Agent, or Firm*—Benjamen E. Kern (57) ABSTRACT

Methods, systems, and apparatuses are provided for generation of focused stress waves that selectively apply tensile stress to local regions of a bonded article.

22 Claims, 4 Drawing Sheets

U.S. PATENT DOCUMENTS

| | | | |
|---|---|---|---|
| 6,759,626 | B2 | 7/2004 | Clauer et al. |
| 6,848,321 | B2 | 2/2005 | Bossi et al. |
| 6,945,114 | B2 | 9/2005 | Kenderian et al. |
| 7,131,331 | B2 | 11/2006 | Bates |
| 7,150,193 | B2 | 12/2006 | Lorraine et al. |
| 7,154,067 | B2 | 12/2006 | Yoshii |
| 7,253,908 | B2 | 8/2007 | Vaccaro et al. |
| 7,270,004 | B2 | 9/2007 | Dickinson et al. |
| 7,509,876 | B1 * | 3/2009 | Sokol et al. .................... 73/827 |
| 2004/0224179 | A1 * | 11/2004 | Sokol et al. ................. 428/610 |
| 2005/0120803 | A1 | 6/2005 | Sokol et al. |
| 2008/0257048 | A1 | 10/2008 | Walters et al. |

OTHER PUBLICATIONS

Applicant notes the existence of associated, co-pending application, Walters, et al , "Apparatus and Method for Non-Destructive Testing", U.S. Appl. No. 11/227,745, filed Sep. 15, 2005.

Applicant notes the existence of associated, co-pending application, Sokol, et al , "Laser Bond Inspection Using Annular Laser Beam", U.S. Appl. No. 11/873,677, filed Oct. 17, 2007.

Toller, et al., "Tape Overlay for Laser Bond Inspection", U.S. Appl. No. 11/873,705, filed Oct. 17, 2007.

Sokol, et al., "Lamb Waves for Laser Bond Inspection", U.S. Appl. No. 11/873,571, filed Oct. 17, 2007.

* cited by examiner

LASER BOND INSPECTION USING ANNULAR LASER BEAM

CROSS-REFERENCE TO RELATED APPLICATIONS

This application is a continuation application of U.S. patent application Ser. No. 11/873,677, filed Oct. 17, 2007, which is hereby incorporated by reference in its entirety.

BACKGROUND

A need exists in industry for non-destructive inspection (NDI) of composite structures assembled with adhesive bonds. Among other techniques, laser bond inspection (LBI) has proven useful. Normally, LBI involves depositing laser energy onto the front surface of a bonded article and generating compression waves that reflect off of the back surface of the bonded article as tensile waves. The tensile waves predominantly provide the stresses that interrogate the bond. In the simplest form of LBI, the laser energy is deposited uniformly onto a circular area on a bonded article's exposed surface. The energy deposition results in a series of alternating compression and tension waves that propagate into the bonded article. These waves reflect from the back surface, or other impedance discontinuities, of the bonded article, and interact with one another to produce regions of varying tensile stress. If a tensile wave of sufficient strength encounters a weak bond, the bond will fail (or disbond). The variation in peak tensile stress with depth in the bonded article depends, in part, on the ratio of the beam diameter to the thickness of the bonded article.

The disbonded interface may be detected by ultrasound after the laser exposure, or by techniques used simultaneously with laser exposure, such as a velocity interferometer for surfaces of any reflectance (VISAR), an electromagnetic acoustic transducer (EMAT), capacitance probes, or piezoelectric ultrasonic transducers (UT).

If a bond in a thick bonded article (e.g., >¼ inch) is near the front surface where the laser energy is applied, high fluences may be required for interrogation because the interrogating tensile wave must have sufficient amplitude to stress the bond adequately after the initial compressive and reflected tensile waves have traveled nearly twice the thickness of the bonded article. Material failure may occur at the back surface (spalling) at fluences that are still inadequate (due to stress wave attenuation) to properly stress the bond near the front surface.

A similar problem occurs when attempting to interrogate a particular bond near the front surface of a bonded article having two or more bonds. The fluences required to stress the bond of interest near the front surface may undesirably damage good laminate bond(s) nearer the back surface.

SUMMARY

In one embodiment, a method is provided for testing bond strength of a bond in a bonded article having a front surface, a back surface, and a thickness, the method comprising: positioning a laser source near the front surface; depositing laser energy onto the front surface in the form of an annular laser beam, wherein the annular laser beam has an inner diameter and an outer diameter, and wherein the laser energy is contained substantially within the outer diameter, and wherein depositing the laser energy results in the generation of alternating compression and tension waves that produce regions of varying tensile stress; adjusting a ratio of the inside diameter to the outside diameter and/or the ratio of the outside diameter to the thickness to concentrate the tensile stress at or near the bond; and measuring surface motions.

In another embodiment, a method for laser bond inspection of a bonded article is provided, the method comprising: subjecting the bonded article to an annular laser beam having an energy rich outer diameter having a size and an energy deficient inner diameter having a size; adjusting the size of the outer diameter relative to the size of the inner diameter to select a depth of inspection; and detecting bond failure at the selected depth.

In yet another embodiment, a method is provided for selectively testing a particular bond of a bonded article having two or more bonds, the method comprising: exposing a surface of the bonded article to an annular laser beam having an outer portion having a first area and an inner portion having a second area, the outer portion containing laser energy, wherein the exposing causes a series of alternating compression waves and tension waves that result in regions of varying tensile stress; and adjusting the first area relative to the second area to concentrate the tensile stress at the particular bond.

In one embodiment, a system for measuring bond strength is provided, comprising: a laser source capable of depositing an annular laser beam onto a bonded assembly having a thickness, the annular laser beam having an outer diameter and an inner diameter, wherein the ratio of the outer diameter to the inner diameter and/or the ratio of the outer diameter to the thickness can be adjusted, and wherein the outer diameter contains laser energy; wherein the laser source is positioned near the bonded assembly and activated to generate alternating compression and tension waves that produce regions of tensile stress, and wherein the ratio of the outer diameter to the inner diameter and/or the ratio of the outer diameter to the thickness are adjusted to concentrate the tensile stress at a selected location within the bonded assembly; and a surface motion detector.

In another embodiment, a system for interrogating a bond in an article is provided, the system comprising: an irradiation device configured to irradiate the article to induce the generation of stress wave activity in the article, the irradiation device being further capable of depositing an annular laser beam onto the article, the annular laser beam having an outer diameter and an inner diameter, and wherein the irradiation device is capable of adjusting the ratio of the outer diameter to the inner diameter and/or the ratio of the outer diameter to a thickness of the article; and a detector configured to detect surface motion indicative of stress wave activity generated in the article.

BRIEF DESCRIPTION OF THE DRAWINGS

The accompanying figures, which are incorporated in and constitute a part of the specification, illustrate various example systems, methods, results, and so on, and are used merely to illustrate various example embodiments. It should be noted that various components depicted in the figures may not be drawn to scale, and that the angles and interferences depicted in the figures are presented for purposes of illustration only, and should not be considered in any way as limiting.

DETAILED DESCRIPTION

The present embodiments disclose methods, systems, and apparatuses for generation of focused stress waves that selectively apply tensile stress to local regions of a bonded article. The present embodiments will find use in any field in which non-destructive bond inspection is required or desired.

In one embodiment, a method is provided for testing bond strength of a bond in a bonded article having a front surface, a back surface, and a thickness, the method comprising: positioning a laser source near the front surface; depositing laser energy onto the front surface in the form of an annular laser beam, wherein the annular laser beam has an inner diameter and an outer diameter, and wherein the laser energy is contained substantially within the outer diameter, and wherein depositing the laser energy results in the generation of alternating compression and tension waves that produce regions of varying tensile stress; adjusting a ratio of the inside diameter to the outside diameter and/or the ratio of the outside diameter to the thickness to concentrate the tensile stress at or near the bond; and measuring surface motions. Of course, one of ordinary skill in the art will readily recognize that the proximity and/or orientation of the laser source relative to the bonded article may vary, and may be any operable or workable range and/or displacement.

In one embodiment, the method may further comprise applying a substantially opaque overlay to the front surface of the bonded article and providing a substantially transparent medium onto the opaque overlay. In another embodiment, the method may further comprise selectively varying the laser energy. In one embodiment, the surface motions are measured by a laser interferometer. In another embodiment, the bonded article is greater than or equal to ¼ inch thick and the bond is closer to the front surface than to the back surface. In yet another embodiment, the bonded article contains two or more bonds.

In another embodiment, a method for laser bond inspection of a bonded article is provided, the method comprising: subjecting the bonded article to an annular laser beam having an energy rich outer diameter having a size and an energy deficient inner diameter having a size; adjusting the size of the outer diameter relative to the size of the inner diameter to select a depth of inspection; and detecting bond failure at the selected depth. In one embodiment, the detecting comprises detecting with an ultrasonic transducer. In another embodiment, the bonded article is greater than or equal to ¼ inch thick and the selected depth is proximate to the surface being subjected to the annular laser beam. In another embodiment, the bonded article contains two or more bonds.

Figure 1:
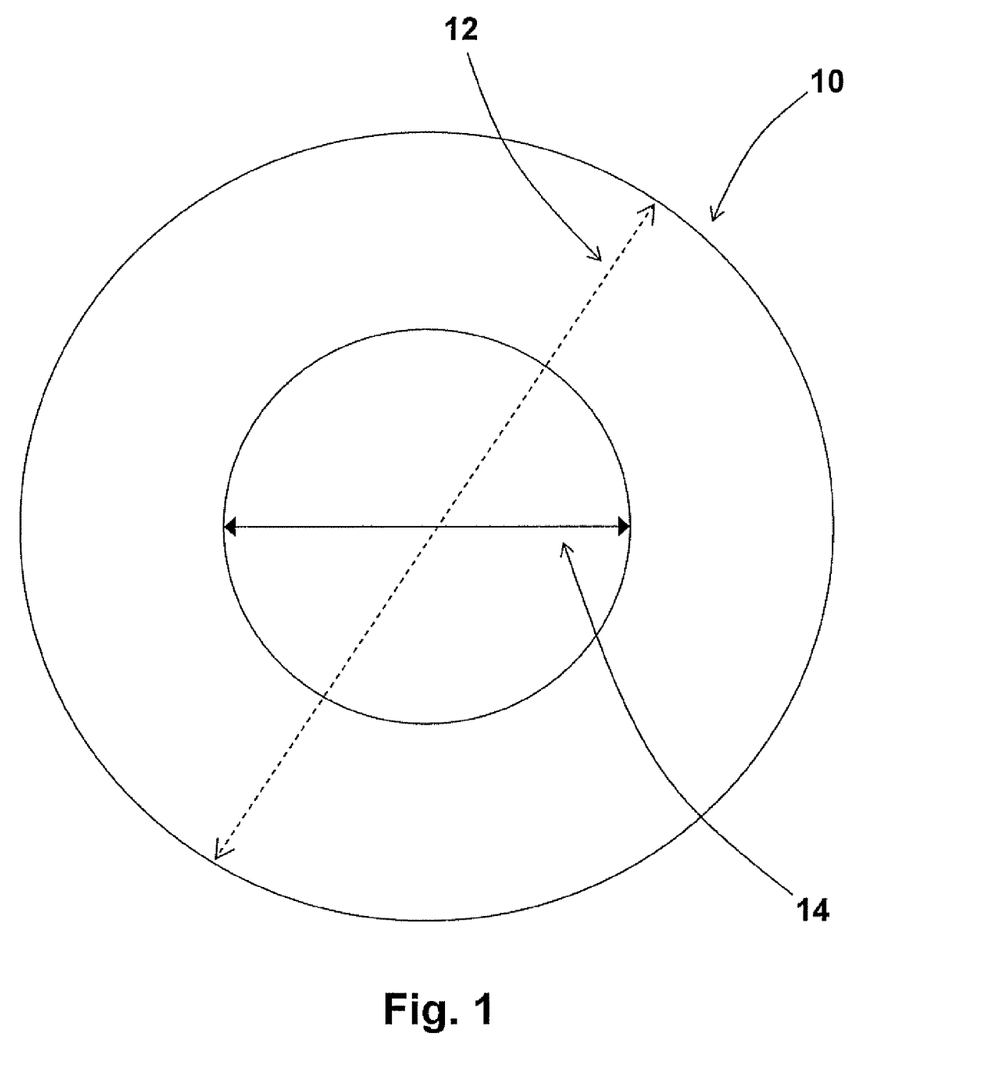
FIG. 1 illustrates an exemplary embodiment of an annular laser beam

With reference to FIG. 1, laser energy in an annular laser beam 10 is predominantly or entirely contained within the outer ring (or outer diameter) 12 surrounding the center (or inner diameter) 14 of annular laser beam 10. Relatively little or no laser energy is contained within the center 14 of annular laser beam 10.

Generation of such an annular laser beam may include, for example, placement of a central, circular obscuration in a circular laser beam prior to focusing the beam. The laser beam source may be any source known in the art. The annular laser beam may also be a part of a laser shock processing assembly. Suitable exemplary laser shock processing assemblies and methods are described in U.S. Pat. Nos. 5,741,559, 5,911,891, 6,412,331, 5,131,957, and U.S. application Ser. No. 10/950,865, each of which is incorporated by reference herein in its entirety.

The disbonded interface may be detected by, for example, conventional ultrasound after the laser exposure or by techniques used simultaneously with laser exposure, such as a velocity interferometer for surfaces of any reflectance, an electromagnetic acoustic transducer, capacitance probes, or piezoelectric ultrasonic transducers.

In accordance with the present embodiments, the annular laser beam may be used to concentrate the peak tensile stress near the bond line of interest. The alternating sequence of compression and tension waves results from the finite diameter of the annular laser beam and, thus, the chosen geometry of the annular laser beam can be used to control the location of peak tension. In other words, with reference to FIG. 1, by adjusting the ratio of inner diameter 14 relative to outer diameter 12 of annular laser beam 10, a specific depth of inspection can be selected.

Figure 2:
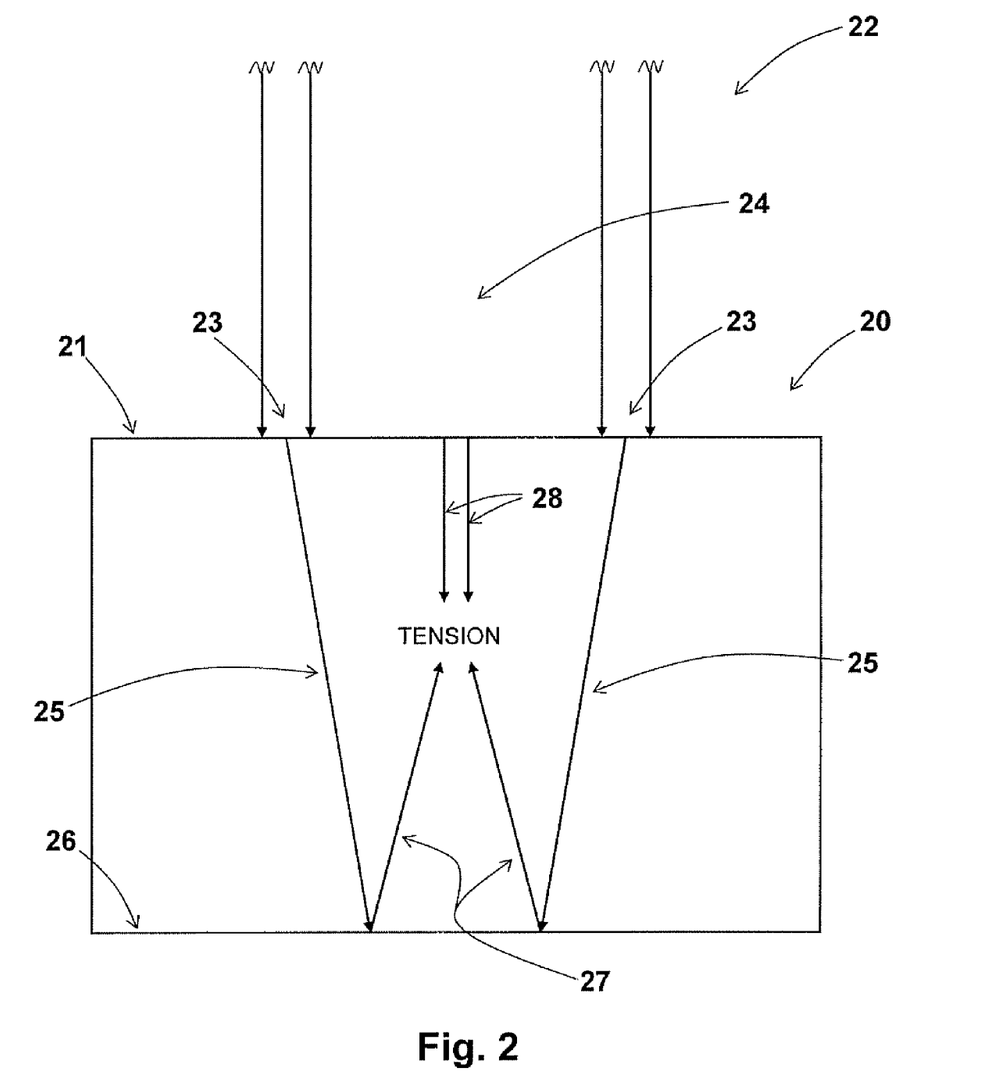
FIG. 2 is an exemplary schematic illustration of a stress wave focusing effect within a bonded article.

FIG. 2 is an exemplary cross-sectional schematic illustration of a stress wave focusing effect within an article FIG. 2 shows schematically how stress waves generated by an annular laser beam exposure pattern may focus to give maximum tensile stress waves at a particular location in the article. For example, front surface 21 of article 20 is struck by annular laser beam 22, having an outer diameter 23 and an inner diameter 24. Primary compression waves 25 are generated, which reflect off of back surface 26 of article 20 as tensile waves 27, which are focused at a particular location depending on the ratio of outer diameter 23 to inner diameter 24 and/or the ratio of the outer diameter 23 to the thickness of article 20.

With further reference to FIG. 2, opposing sides of outer diameter 23 of the annular laser beam 22 each produce an alternating sequence of compression and tension waves in article 20. When the primary compression waves 25 reach the back surface 26 of article 20, they reflect as primary tensile waves 27, which constructively interfere with the secondary tensile waves 28 propagating toward rear surface 26. The interference of primary tensile waves 27 with secondary tensile waves 28 produces a region of enhanced tensile stress at a selected region, depending, again, on the ratio of outer diameter 23 to inner diameter 24 and/or the ratio of the outer diameter 23 to the thickness of article 20.

In yet another embodiment, a method is provided for selectively testing a particular bond of a bonded article having two or more bonds, the method comprising: exposing a surface of the bonded article to an annular laser beam having an outer portion having a first area and an inner portion having a second area, the outer portion containing laser energy, wherein the exposing causes a series of alternating compression waves and tension waves that result in regions of varying tensile stress; and adjusting the first area relative to the second area to concentrate the tensile stress at the particular bond. In one embodiment, the method may further comprise detecting bond failure at the particular bond. In another embodiment, the detecting may comprise electromagnetically detecting a stress wave signature, measuring surface motions with a laser interferometer, or detecting with an ultrasonic transducer. In another embodiment, the method further comprises minimizing or eliminating any damage to bonds other than the particular bond.

Figure 3:
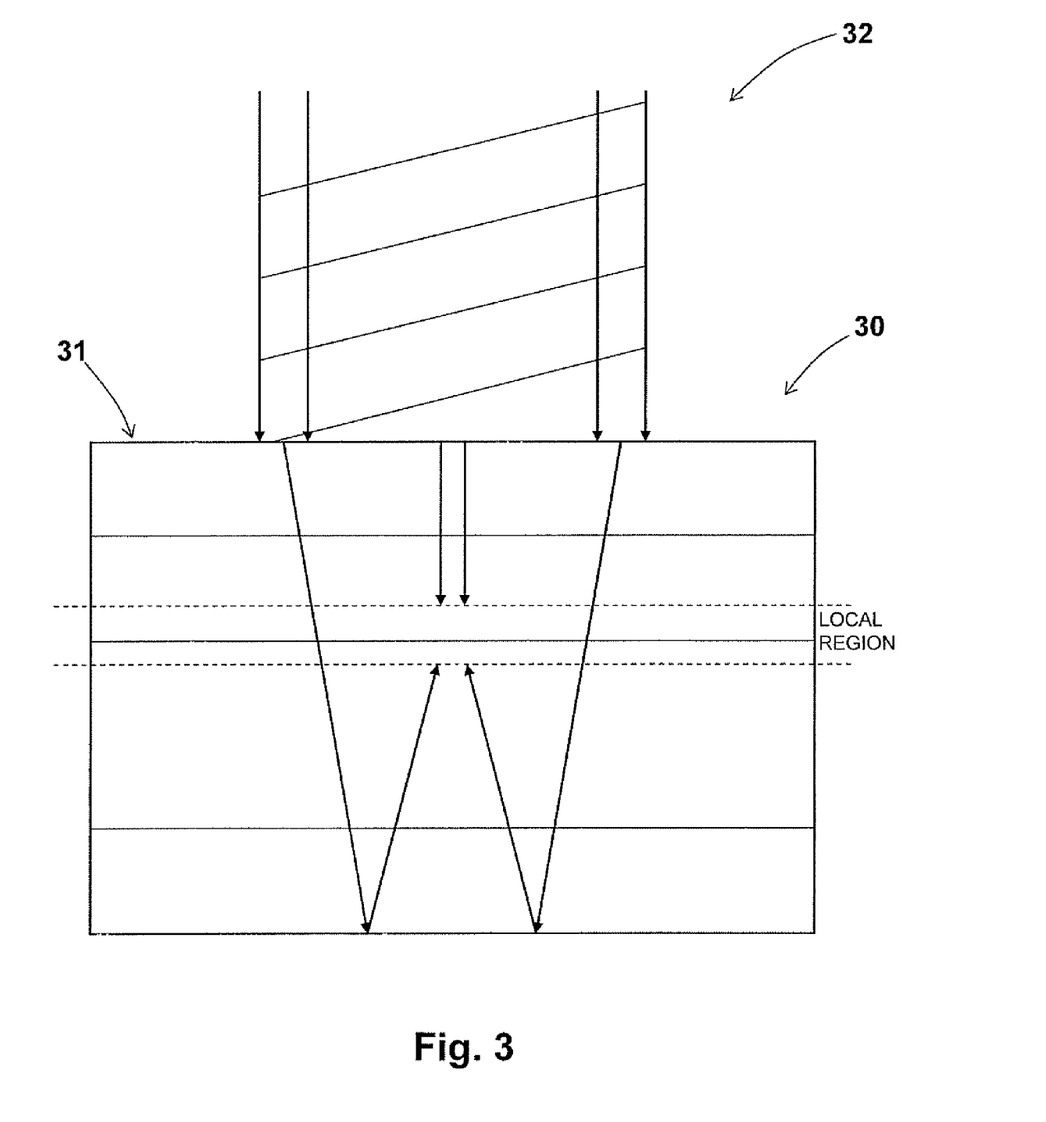
FIG. 3 illustrates an exemplary embodiment of the generation of focused stress waves that selectively apply tensile stress to local regions containing a particular bond of a bonded article having two or more bonds, while minimizing or eliminating damage to other laminate bond(s) disposed within the bonded article.

FIG. 3 illustrates an exemplary embodiment of the generation of focused stress waves that selectively apply tensile stress to local regions containing a particular bond of a bonded article having two or more bonds, while minimizing or eliminating damage to other laminate bond(s) disposed within the bonded article. As shown in FIG. 3, a surface 31 of the multilayer bonded article 30 is exposed to an annular laser beam 32 as described herein. The exposing causes a series of alternating compression waves and tension waves that result in regions of varying tensile stress. By adjusting the ratio of the inner and outer diameters of the annular laser beam and/or the ratio of the outer diameter to the thickness of the bonded article, the tensile stress may be concentrated at a local region containing the particular bond, while minimizing or eliminating damage to other laminate bonds in the bonded article.

In still another embodiment, a method is provided for interrogating a bond in a thick article having a front surface and a back surface, the bond being proximate to the front surface, the method comprising: depositing an annular laser beam over the front surface of the article, thereby causing stress waves in the article, wherein the annular laser beam has an inner diameter and an outer diameter, the inner diameter and the outer diameter defining a ratio therebetween, the outer diameter having laser energy; and adjusting the ratio of the inner diameter to the outer diameter to focus the stress waves at or near the bond. In one embodiment, the method further comprises detecting bond failure. In another embodiment, the detecting comprises detecting by electromagnetically detecting a stress wave signature, measuring surface motions with a laser interferometer, or detecting with an ultrasonic transducer. In another embodiment, the method further comprises minimizing or eliminating any damage to the back surface of the article.

Figure 4:
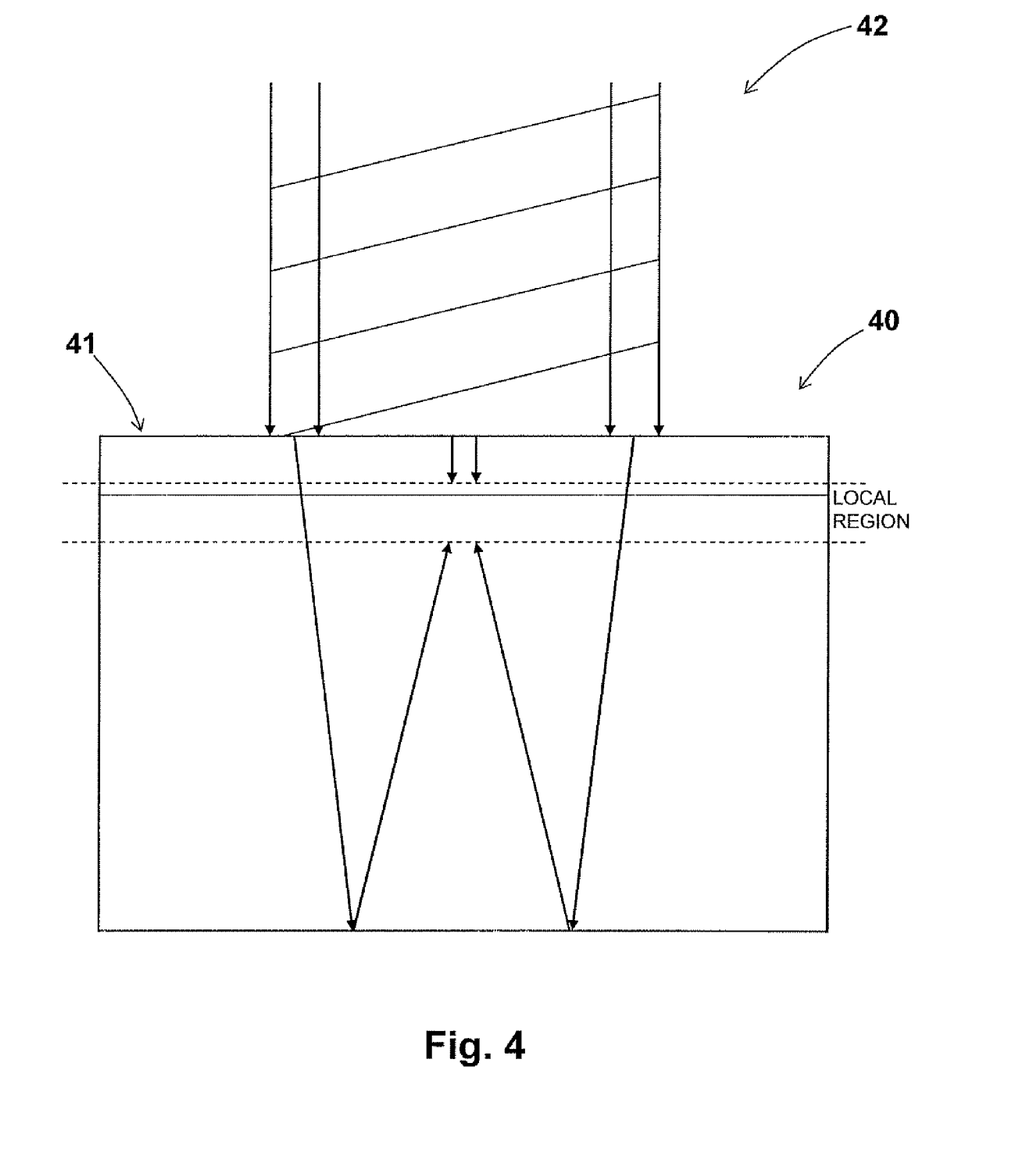
FIG. 4 illustrates an exemplary embodiment of the generation of focused stress waves that selectively apply tensile stress to local regions of a thick bonded article containing a bond which is proximate to an exposed surface of the thick bonded article, while minimizing or eliminating damage to an unexposed surface of the thick bonded article.

FIG. 4 illustrates an exemplary embodiment of the generation of focused stress waves that selectively apply tensile stress to local regions of a thick bonded article containing a bond which is proximate to an exposed surface of the thick bonded article, while minimizing or eliminating damage to an unexposed surface of the thick bonded article. As shown in FIG. 4, a surface 41 of the thick bonded article 40 is exposed to an annular laser beam 42 as described herein. The exposing causes a series of alternating compression waves and tension waves that result in regions of varying tensile stress. By adjusting the ratio of the inner diameter to the outer diameter of the annular laser beam 42 and/or the ratio of the outer diameter to the thickness of the thick bonded article, the tensile stress may be concentrated at a local region containing the bond, while minimizing or eliminating damage to the back surface of the thick bonded article.

In one embodiment, a system for measuring bond strength is provided, comprising: a laser source capable of depositing an annular laser beam onto a bonded assembly having a thickness, the annular laser beam having an outer diameter and an inner diameter, wherein the ratio of the outer diameter to the inner diameter and/or the ratio of the outer diameter to the thickness can be adjusted, and wherein the outer diameter contains laser energy; wherein the laser source is positioned near the bonded assembly and activated to generate alternating compression and tension waves that produce regions of tensile stress, and wherein the ratio of the outer diameter to the inner diameter and/or the ratio of the outer diameter to the thickness are adjusted to concentrate the tensile stress at a selected location within the bonded assembly; and a surface motion detector.

In another embodiment, a system for interrogating a bond in an article is provided, the system comprising: an irradiation device configured to irradiate the article to induce the generation of stress wave activity in the article, the irradiation device being further capable of depositing an annular laser beam onto the article, the annular laser beam having an outer diameter and an inner diameter, and wherein the irradiation device is capable of adjusting the ratio of the outer diameter to the inner diameter and/or the ratio of the outer diameter to a thickness of the article; and a detector configured to detect surface motion indicative of stress wave activity generated in the article.

In one embodiment, the outer diameter contains laser energy. In another embodiment, the system may further comprise a processor to determine integrity of the bond. The irradiation device may be a laser. The laser may be configured to laser bond inspect the article. In one embodiment, the system may further comprise: a first applicator to apply a substantially opaque overlay to the article; and a second applicator to provide a substantially transparent medium onto the opaque overlay. In another embodiment, the system may further comprise a controller configured to activate the laser in a pulsing operation. In another embodiment, the controller or the laser oscillator configuration may be further configured to selectably vary laser pulse width. In one embodiment, variation of the laser pulse width enables selective control of a duration of shockwave activity present in the article as a result of the laser bond inspection. In one embodiment, the system may further comprise a controller to control operation of the laser, the controller being configured to selectably vary laser energy.

In one embodiment, an apparatus is provided for use with an article having a bond disposed therein, the apparatus comprising: a laser shock processing assembly configured to laser bond inspect the article, wherein the laser shock processing assembly is configured to deliver an annular laser beam onto a surface of the article, the annular laser beam having an outer diameter and an inner diameter, wherein the laser shock processing assembly is capable of adjusting the ratio of the outer diameter to the inner diameter and/or the ratio of the outer diameter to the thickness of the article; and a detector configured to detect bond failure. In one embodiment, the detector may be an electromagnetic acoustic transducer configured to detect a stress wave signature emanating from the article. In another embodiment, the outer diameter contains laser energy.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

The following examples are provided to illustrate various embodiments and shall not be considered as limiting in scope.

EXAMPLE

An annular laser beam with 14 mm outside diameter and 7 mm inside diameter was incident on a 20.5 mm (0.81 inch) thick BMS 8-276 composite coupon with a water-black-paint (WBP) overlay. The pulse width was nominally 100-300 ns and the fluence was varied. The focusing effect was observed when the paint spalled off the back surface of the coupon in a small circular area centered on the beam axis directly under the open area of the beam exposure pattern where no fluence was delivered. A solid beam at the same fluence (33% more energy) also spalled paint, but onto a much larger, less-well defined area.

The back surface paint spallation effect was very reproducible and the apparent visual differences in the appearance of the spallation caused by the types of beam were a clear indication of annular laser beam, stress-wave focusing. Post UT inspection of the coupon revealed that both the solid and annular laser beams created internal delamination and bond failure, although multiple pulses on the same spot were required in some cases, due to stress waive attenuation in the article.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" or "having" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995)

What is claimed is:

1. A method for testing bond strength of a bond in a bonded article having a front surface, a back surface, and a thickness, comprising:
    positioning a laser source near the front surface;
    depositing laser energy onto the front surface in the form of an annular laser beam, wherein the annular laser beam has an inner diameter and an outer diameter, each having a laser energy greater than 0 J, the laser energy in the outer diameter being greater than the laser energy in the inner diameter; and
    measuring surface motions.

2. The method of claim 1, further comprising applying a substantially opaque overlay to the front surface and providing a substantially transparent medium over the opaque overlay.

3. The method of claim 1, further comprising selectively varying the laser energy.

4. The method of claim 1, wherein the measuring comprises measuring with a laser interferometer.

5. The method of claim 1, wherein the bonded article is greater than or equal to ¼ inch thick and the bond is closer to the front surface than to the back surface.

6. The method of claim 1, wherein the bonded article contains two or more bonds.

7. A method for laser bond inspection of a bonded article having a thickness, the method comprising:
    selecting a size of an outer diameter and a size of an inner diameter, thereby selecting a depth of inspection;
    generating an annular laser beam having the outer diameter and the inner diameter, the outer diameter having a higher energy content and the inner diameter having a lower energy content, each energy content being greater than zero Joules;
    subjecting a surface of the bonded article to the annular laser beam; and
    detecting bond failure at the selected depth.

8. The method of claim 7, wherein the detecting comprises detecting with an ultrasonic transducer.

9. The method of claim 7, wherein the thickness is greater than or equal to ¼ inch and the selected depth is proximate to the surface being subjected to the annular laser beam.

10. The method of claim 7, wherein the bonded article contains two or more bonds.

11. A method for selectively testing a particular bond in a bonded article having two or more bonds, comprising:
    generating an annular laser beam; and
    exposing a surface of the bonded article to the annular laser beam, the annular laser beam having an outer portion and an inner portion, the outer portion having a first energy which is greater than 0 J and the inner portion having a second energy which is greater than 0 J, the first energy being greater than the second energy.

12. The method of claim 11, further comprising detecting bond failure at the particular bond.

13. The method of claim 12, wherein the detecting comprises electromagnetically detecting a stress wave signature, measuring surface motions with a laser interferometer, or detecting with an ultrasonic transducer.

14. The method of claim 11, further comprising minimizing or eliminating any damage to bonds other than the particular bond.

15. A system for measuring bond strength, comprising:
    a laser source capable of depositing an annular laser beam onto a bonded assembly having a thickness, the annular laser beam having an outer diameter and an inner diameter, each having an energy greater than 0 J, the energy of the outer diameter being greater than the energy of the inner diameter;
    wherein the laser source is positioned near the bonded assembly and activated to generate alternating compression and tension waves that produce regions of tensile stress; and
    a surface motion detector.

16. A system for interrogating a bond in an article, comprising:
    an irradiation device configured to irradiate the article to induce generation of stress wave activity in the article, the irradiation device being capable of depositing an annular laser beam onto the article, the annular laser beam having an outer diameter and an inner diameter, the outer diameter containing a higher energy than the inner diameter, the inner diameter having an energy greater than 0 J; and a detector configured to detect surface motions indicative of stress wave activity generated in the article.

17. The system of claim 16, further comprising a processor to determine an integrity of the bond.

18. The system of claim 16, wherein the irradiation device is a laser.

19. The system of claim 18, further comprising a controller, the controller being configured to activate the laser in a pulsing operation.

20. The system of claim 19, wherein the controller is further configured to selectably vary a pulse width of the laser.

21. The system of claim 16, wherein the irradiation device is further capable of adjusting a ratio of the outer diameter to a thickness of the article.

22. The system of claim 16, further comprising:

a first applicator to apply a substantially opaque overlay to the article; and a second applicator to provide a substantially transparent medium over the opaque overlay.

\* \* \* \* \*